US00PP34901P2

(12) United States Plant Patent
Shoup

(10) Patent No.: US PP34,901 P2
(45) Date of Patent: Jan. 10, 2023

(54) SHRUB ROSE PLANT NAMED 'ROYAL SUNRISE'

(50) Latin Name: *Rosa hybrida*
Varietal Denomination: Royal Sunrise

(71) Applicant: George Michael Shoup, Brenham, TX (US)

(72) Inventor: George Michael Shoup, Brenham, TX (US)

( * ) Notice: Subject to any disclaimer, the term of this patent is extended or adjusted under 35 U.S.C. 154(b) by 64 days.

(21) Appl. No.: 17/358,672

(22) Filed: Jun. 25, 2021

(51) Int. Cl.
*A01H 5/02* (2018.01)
*A01H 6/74* (2018.01)

(52) U.S. Cl.
USPC ..... Plt./102
CPC ..... *A01H 6/749* (2018.05)

(58) Field of Classification Search
USPC ..... Plt./102
CPC ..... A01H 6/749
See application file for complete search history.

(56) References Cited

U.S. PATENT DOCUMENTS

PP33,507 P2 * 9/2021 Meilland ..... A01H 6/749 Plt./101
2017/0055384 P1 * 2/2017 Olesen ..... Plt./101
2021/0137027 A1 * 5/2021 Howe ..... A01G 9/16

* cited by examiner

*Primary Examiner* — Anne Marie Grunberg

(57) ABSTRACT

A new and distinct variety of shrub rose plant, herein referred to by its cultivar name, 'Royal Sunrise', is provided which abundantly and continuously forms extremely fragrant blooms. The growth habit is bushy and shrub-like. The foliage is smooth, and dark green with a glossy finish. The plant propagates from cuttings easily, has a unique bloom color combination of both purple and yellow. The new variety is well suited to growing as attractive ornamentation and a source of fragrance in in the landscape.

1 Drawing Sheet

Botanical/commercial classification: Latin name—*Rosa hybrida.*

Varietal denomination: 'Royal Sunrise'.

SUMMARY OF THE INVENTION

The new variety of *Rosa hybrida* shrub rose plant was created at Brenham, Tex., U.S.A., by artificial pollination wherein two parents were crossed which previously had been observed in the hope that they would contribute their unique color and fragrance (from the female parent), and disease resistance (in the case of the male parent). The female parent (i.e., the seed parent) was the 'WEKjucistwe' variety (U.S. Plant Pat. No. 31,861.) The male parent (i.e., the pollen parent) was the 'Gideon Lincecum' variety (non-patented).

The parentage of the new variety can be summarized as follows:

'WEKjucistwe' x 'Gideon Lincecum'

The seeds resulting from the above pollination were stratified in an artificial environment and sown into trays in a greenhouse environment. Seedlings were obtained and displayed phenotypic and biological variation. Selective trialing and evaluation of the seedlings resulted in the identification of a single plant of the new variety.

It was found that the new shrub rose plant of the present invention possesses the following combination of characteristics:

(a) abundantly and continuously forms extremely fragrant blooms.
(b) exhibits a bushy and shrub-like growth habit, (c) forms blooms containing a unique color combination of both purple and yellow colors,
(d) forms disease resistant foliage with a smooth and glossy finish,
(e) is well suited for growing as attractive ornamentation and a source of fragrance in in the landscape.

The new rose can be readily distinguished from its ancestors upon inspecting the color of the blossoms. More specifically, the 'Royal Sunrise' variety forms blossoms more saturated in color than both of its parental varieties, 'WEKjucistwe' and 'Gideon Lincecum'. Additionally, the new variety can also be distinguished from its ancestors by inspecting the petal count of the blossoms. More specifically, the 'Royal Sunrise' variety forms blossoms of a higher petal count than parental variety 'Gideon Lincecum', but lower in petal count than parental variety 'WEKjucistwe'.

The new variety of the present invention also can be readily distinguished from other shrub rose plants, including the 'Collicutt' variety (U.S. Plant Pat. No. 8,054) AKA 'Morden Blush', upon inspection of the foliage. More specifically, the 'Royal Sunrise' variety forms dissimilar *Diplocarpon rosae* (black spot) resistant foliage when compared to the 'Collicutt' variety, which forms foliage that is extremely susceptible to black spot.

Asexual reproduction of 'Royal Sunrise' was done by taking rotted cuttings (clones) in Brenham Tex., U.S.A. in beginning in 2019. Cuttings were taken from mature stems that were approximately 10 to 15 cm in length and approximately 0.75 cm in diameter. Initial cuttings were taken of the new variety and grew into mature plants in Brenham, Tex. Subsequent cuttings were taken of the initial asexually reproduced plants and grown into mature plants. Mature plants of both the initially propagated plants and the subsequently propagated plants were compared. There was no observable difference between the generations. Therefore, it was demonstrated that the characteristics of 'Royal Sunrise' remain stable, uniform, and true to type in successive generations of asexual reproduction.

BRIEF DESCRIPTION OF THE DRAWING

The accompanying color illustration shows as true is as is reasonably possible to obtain in color photographs of this type, the typical characteristics of the plant parts, i.e., the flowers, buds, stems and leaves of the new rose, 'Royal Sunrise'. The illustrated rose plant parts were approximately one year of age and were observed during August, while growing on their own roots in Brenham, Tex., U.S.A. Flowers, buds, and stem growth are displayed in various stages of maturity. The upper side and under side of the leaves, blooms and petals are displayed.

DETAILED BOTANICAL DESCRIPTION

The chart used in the identification of colors is The Royal Horticultural Society Colour Chart (R.H.S. Colour Chart) Edition V (2007). The description is based one year old specimens of the new variety during August while growing outdoors on their own roots at Brenham, Tex., U.S.A.

Class: Shrub rose named, 'Royal Sunrise'.

Plant:

*Height*.—Approximately 0.9 to 1.2 meters on average at maturity.

*Width*.—Approximately 0.6 to 0.9 meters on average at maturity.

*Habit*.—Bushy and round.

Stems:

*Size*.—Approximately 18 cm tall by 1.1 cm in caliper.

*Color*.—Young stems: Green Group 137A to B. Adult wood: Yellow-Green Group 146C.

*Prickles*.—Size: Approximately 0.6 cm in length on average. Quantity: Approximately 1 prickle per 15 cm section of stem. Curvature: None detected — straight. Color: Greyed-Orange Group 177B. Density: Sparse.

*Texture*.—Glabrous.

*Internodal spacing*.—Approximately 5 cm on average.

Leaves:

*Arrangement*.—Alternate, odd-pinnate, and compound.

*Margin*.—Doubly serrate.

*Stipules*.—Size: Approximately 17 mm×7 mm on average. Margin: Adnate with winged tips and ciliate edges. Color: Green Group 135A. Texture: Slightly pubescent.

*Size*.—Approximately 15.5 cm×10 cm on average.

*Petioles*.—Upper surface: Yellow-Green Group 146B. Under surface: Green Group 143C. Size: Approximately 6.4 cm×1.4 mm on average. Shape: Filiform.

*Glossiness of the upper side of the leaf*.—Strong.

*Rachis*.—Color: Green Group 143C.

*Leaflets*.—Number: 5 and 7. Shape: Ovate, with an acute apex and rounded base. Size: Approximately 5 cm×3.25 cm on average. Venation: Reticulate. Venation Color: Green Group 135A. Apex: Acute. Base: Rounded. Overall appearance: Dark-green and slightly glossy. Undulation of Margin: Medium. Texture Upper Surface: Slightly waxy. Texture Under Surface: Matte. Color (young foliage) upper surface: Yellow-Green Group 146A. Color (young foliage) under surface: Greyed-Red Group 178A. Color (adult foliage) upper surface: Green Group 135A. Color (adult foliage) under surface: Green Group 138A.

Inflorescence:

*Average size of inflorescence*.—Approximately 12 cm by 8 cm on average.

*Number of flowers per inflorescence*.—Approximately 5 to 9 on average.

*Florescence type*.—Paniculate.

*Peduncle*.—Color: Yellow-Green Group 143B. Length: Approximately 4 cm in length on average. Width: 2 mm in width on average. Texture: Slightly pubescent.

*Sepals*.—Number: 5. Size: Approximately 2.1 cm×0.6 cm on average. Arrangement: Pentamerous and imbricate. Shape: Obcunate. Margin: Entire. Sepal Extensions: Weak. Apex: Acuminate. Base: Truncate. Texture: Slightly pubescent. Upper surface: Yellow-Green Group 146B to C. Under surface: Yellow-Green Group 146B to C.

*Buds*.—Shape: Globular (as illustrated). Size: Approximately 2.5 cm in length and 2 cm in width on average. Color (when opening) upper surface: Yellow Group 9A. Color (when opening) under surface: Yellow Group 2B at the base and when exposed to sunlight causes a transition to Red Group 51A, then to Greyed-Purple Group 187D, and finally to Violet-Blue Group N89A to N89B at the apex.

Flower:

*Form*.—Rounded Rosette.

*Shape*.—Flattened orbicular when open.

*Profile of the lower part of the flower*.—Convex.

*Diameter*.—Approximately 5 cm to 6 cm on average.

*Color*.—(When opening) upper surface: Yellow Group 9A at the base and fading to Yellow Group 10B and when exposed to sunlight causes a transition to Violet-Blue Group N89A to B at the apex. (When opening) under surface: Yellow Group 11B at the base and when exposed to sunlight causes a transition to Red Group 54A to Greyed-Purple Group 186A, and finally to Violet-Blue Group N89A to B at the apex. (When blooming) upper surface: Yellow Group 9A at the base and fading to Yellow Group 11B and when exposed to sunlight causes a transition to Violet-Blue Group N89A to B at the apex. (When blooming) under surface: Yellow Group 9A at the base and fading to Yellow Group 10B and when exposed to sunlight causes a transition to Violet-Blue Group N89A to B at the apex. (End of blooming) upper surface: Yellow-White Group 158B to C at the base fading to Violet Group 85A at the apex. (End of blooming) under surface: Violet Group 84C.

*Fragrance*.—Blend of musk, citrus, apple, and guava.

*Petals*.—Petal Size: Approximately 2.5 cm×2.75 cm on average. Petal Shape: Nearly orbicula. Petal Number: Approximately 65 on average. Petal Reflex: Independent (one by one) and slight undulation. Petal Incision: Slight. Petaloids: None present. Petal Drop: Very easily and cleanly after blooming. Apex: Mucronate. Base: Rounded. Margin: Entire with a slight degree of petal margin reflex. Texture: Glabrous. Basal Spot: Absent.

*Lasting quality*.—On plant: Approximately 3 to 4 days on average. In vase: Unknown.

*Petal drop*.—Easily and cleanly after blooming.

*Stamen number*.—Approximately 40 on average.

*Anther color*.—Yellow-Orange Group 21A.

*Anther shape*.—Oblong.

*Anther length*.—Approximately 2.1 mm on average.

*Filament color*.—Yellow-Orange Group 14B.

*Filament length*.—Approximately 2.5 mm on average.

*Pollen quantity*.—Medium amount of pollen produced.

*Pollen color*.—Yellow Group 13B.

*Pistil form*.—Separate and free.

*Pistil number*.—Approximately 40 on average.

*Stigma color*.—Yellow-Orange Group 22A.

*Style color*.—Greyed-Orange Group 163D.

*Style length*.—Approximately 2 mm on average.

*Receptacle*.—Achenes form on the inside of the fruit. Size: Approximately 0.5 cm×0.5 cm on average when mature.

*Rate of flower opening*.—Fast.

*Blossoming*.—Continuous.

*Lasting quality*.—On plant: Approximately 3 to 4 days on average. In vase: Unknown.

Development:

*Vegetation*.—Lush with average vigor.

*Growth rate*.—Average growth rate.

*Hip/seed formation*.—A medium number of hips that are round in shape with a flat top are formed after blossoming. Ripe coloration of hips is 31A-30C.

Root system:

*Root color*.—Yellow-White Group 158D.

*Root habit*.—Well rounded.

Physiology:

*Disease resistance*.—Resistant to most races of *Diplocarpon rosae* (black spot), and above average resistance to *Podosphaera pannosa* (powdery mildew). The variety displays an intermediate resistance to *Peronospora sparsa* (downy mildew).

*Cold hardiness*.—The variety has been found to be suitable for climactic conditions in USDA Plant Hardiness Zone 8. Based on the performance of the parental varieties, it is likely, although untested, that the new variety is also suitable for climatic conditions of USDA Plant Hardiness Zones 5, 6 and 7.

*Heat tolerance*.—The variety exhibits average heat tolerance. The variety has been found to be suitable for climactic conditions in USDA Plant Hardiness Zone 8. Based on the performance of its parent varieties, it is likely, although untested, that the new variety is also suitable for climatic conditions of USDA Plant Hardiness Zone 9.

*Drought tolerance*.—The variety exhibits average drought tolerance.

I claim:

1. A new and distinct shrub rose plant characterized by the following combination of characteristics:

1) abundantly and continuously forms extremely fragrant blooms,
2) exhibits a bushy and shrub-like growth habit,
3) forms blooms containing a unique color combination of both purple and yellow colors,
4) forms disease resistant foliage with a smooth and glossy finish,
5) is well suited for growing as attractive ornamentation and a source of fragrance in in the landscape, substantially as herein illustrated and described.

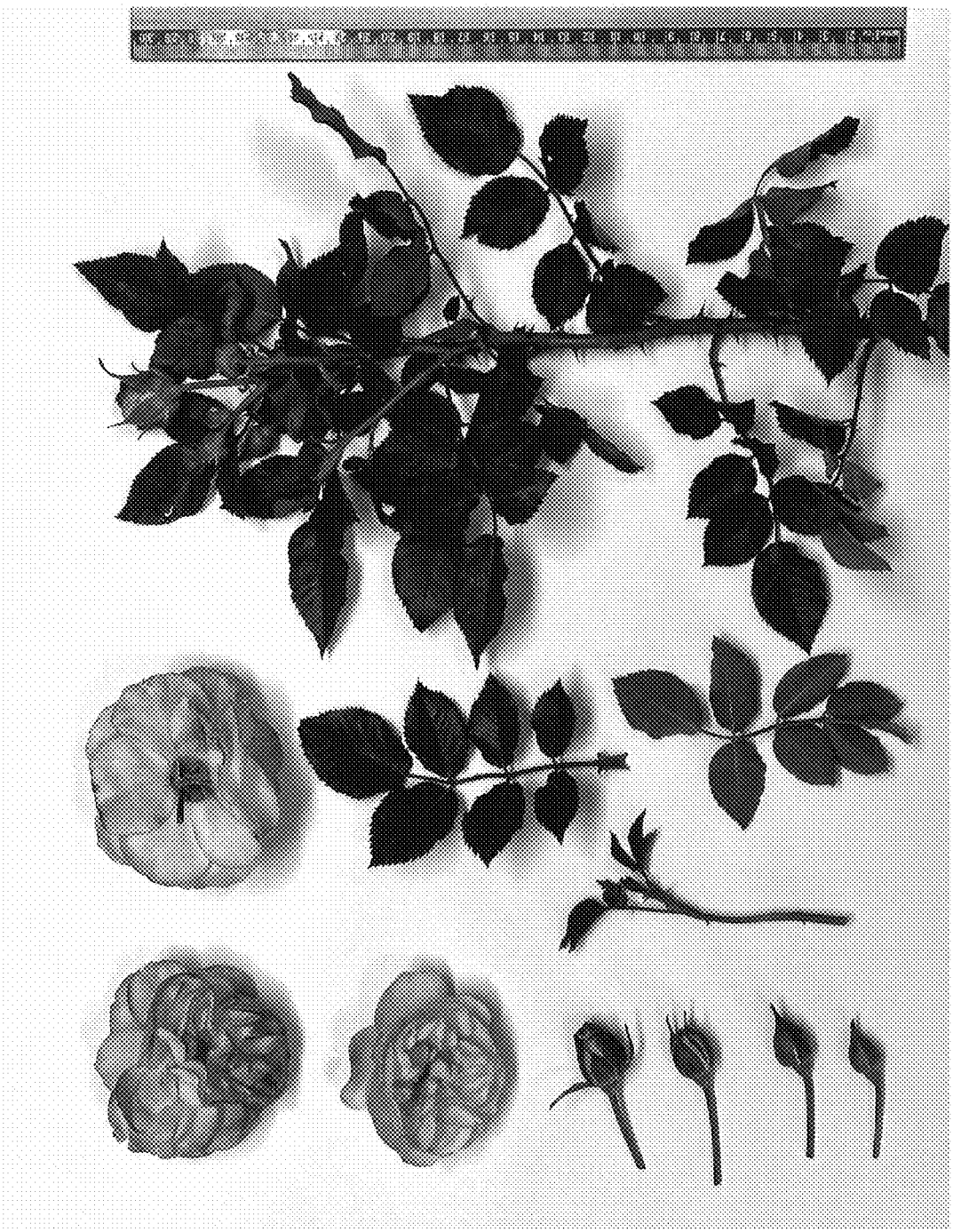

* * * * *